(12) United States Patent
Mahan et al.

(10) Patent No.: US 6,342,230 B1
(45) Date of Patent: Jan. 29, 2002

(54) MATERIALS AND METHODS FOR PREVENTION OR REDUCTION OF THE SEVERITY OF HEARTWATER

(75) Inventors: Suman M. Mahan, Harare (ZW); Anthony F. Barbet, Archer; Michael J. Burridge, Gainesville, both of FL (US); Gillian E. Smith, Harare (ZW)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/465,598

(22) Filed: Dec. 17, 1999

(51) Int. Cl.[7] ................................................ A61K 39/02
(52) U.S. Cl. .................... 424/234.1; 435/243; 435/261; 435/252.1; 424/269.1
(58) Field of Search ........................... 424/234.1, 269.1; 435/243, 261, 252.1

(56) References Cited

PUBLICATIONS

Totté, P., D. McKeever, D. Martinez, A. Bensaid (1997) "Analysis of T–Cell Responses in Cattle Immunized against Heartwater by Vaccination with Killed Elementary Bodies of *Cowdria ruminantium*" *Infection and Immunity* 65(1):236–241.

Mahan, S.M., M. Sileghem, G.E. Smith, B. Byrom (1996) Neutralization of bovine Concanavalin–A T cell supernatant–mediated anti–*Cowdria ruminantium* activity with antibodies specific to Interferon gamma but not to tumor necrosis factor.

Martinez, D., J.C. Maillard, S. Coisne, C. Sheikboudou, A. Bensaid (1994) "Protection of goats against heartwater acquired by immunisation with inactivated elementary bodies of *Cowdria ruminantium*" *Veterinary Immunology and Immunopathology* 41:153–163.

Martinez, D., J.M. Perez, C. Sheikboudou, A. Debus, A. Bensaid (1996) "Comparative efficacy of Freund's and Montanide ISA50 adjuvants for the immunisation of goats against heartwater with inactivated *Cowdria ruminantium*" *Veterinary Parasitology* 67:175–184.

Mahan, S.M., N. Tebele, D. Mukwedeya et al. [1993]*J. Clin. Microbiol.* 31:2729–2737.

Mahan, S.M. et al. [1994] *Infect. Immun.* 62:747–750.

Mahan, S.M., D. Kumbula, M.J. Burridge, A.F. Barbet [1998]"The inactivated *Chowdria ruminantium* vaccine for heartwater protects against heterologous strains and against laboratory and field tick challenge" *Vaccine* 16(11/12):1203–1211.

Totté et al. [1996] *Vet. Immunol. Immunopathol.* 53:61–71.

Mahan, S.M., H.R. Andrew, N. Tebele, M.J. Burridge, A.F. Barbet [1995] "Immunisation of sheep against heartwater with inactivated *Cowdria ruminantium*" *Research in Veterinary Science* 58:46–49.

*Primary Examiner*—Jennifer E. Graser
(74) *Attorney, Agent, or Firm*—Saliwanchik, Lloyd & Saliwanchik

(57) ABSTRACT

The present invention pertains to materials and methods for preventing, or reducing the severity of, heartwater disease in animals. One aspect of the invention is a vaccine against heartwater comprising cultured inactivated *Cowdria ruminantium* rickettsiae mixed with a suitable adjuvant. The vaccine of the subject invention can be injected into an animal and, once injected, induces immune responses which protect the animal from severe heartwater when exposed to infection with *Cowdria ruminantium* rickettsiae. The invention further concerns methods of producing a vaccine for use against heartwater. The invention also concerns methods for inducing an immune response in animals, such as mammals, against heartwater by inoculating an animal with a vaccine composition of the present invention.

8 Claims, No Drawings

MATERIALS AND METHODS FOR PREVENTION OR REDUCTION OF THE SEVERITY OF HEARTWATER

The subject invention was made with government support under a research project supported by United States Agency for InternationalDevelopment Grant No. LAG-1328-G-00-3030-00. The government has certain rights in this invention.

FIELD OF THE INVENTION

This invention relates to vaccine against a rickettsial disease called heartwater, to a rickettsia used in the preparation of said vaccine, to a method of producing a said vaccine, and to a method of vaccinating mammals and, in particular, domestic and wild ruminants.

BACKGROUND OF THE INVENTION

Rickettsiae are non-motile bacteria which depend on the intracellular milieu of host cells for growth and are capable of infecting mononuclear and endothelial cells. As a result, they were initially considered to occupy a special taxonomic niche between viruses and bacteria but are now classified within the bacteria.

Rickettsiae are transmitted to mammals by arthropod vectors such as lice, ticks, and mites. They are responsible for a variety of diseases including typhus, Rocky Mountain spotted fever, and rickettsial pox. In southern Africa, tick bite fever and heartwater are common rickettsial diseases. As a result of their dependence on the intracellular milieu of their host cells for growth, it is difficult to treat rickettsial infections. To enable a host mammal to develop immunity against this infection, bacteriostatic antibiotics are used. These include the tetracycline group of antibiotics and the chloramphenicols.

Heartwater is an economically important disease of domestic ruminants caused by the rickettsia *Cowdria ruminantium* and transmitted by Amblyomma tick species. Heartwater is a constraint to livestock production because it can cause mortality rates of 20–80% in susceptible animals.

Currently, there is only one method of vaccination of domestic animals against heartwater. This method involves infection of the animal intravenously with live virulent *Cowdria ruminantium* rickettsiae followed by treatment with tetracycline antibiotics when clinical disease is manifested. The treated animal then develops immunity to heartwater. However, if treatment is too early the animal fails to become immunized and, if it is treated too late, death can occur. This method of vaccination is both laborious and expensive and is accompanied by considerable risk and uncertainty. Hence a vaccine that is easy to administer, is inactivated and induces protection against mortality would have a major impact on livestock production in areas of the world that are affected by this disease, namely sub-Saharan Africa and the eastern Caribbean. Such a vaccine would have wide-scale application if it did not require stringent handling, transportation, and storage conditions.

BRIEF SUMMARY OF THE INVENTION

The subject invention provides materials and methods for preventing, or reducing the severity of, heartwater. In accordance with this invention, there is provided a vaccine against heartwater comprising cultured inactivated *Cowdria ruminantium* rickettsiae mixed with a suitable adjuvant. The vaccine of the subject invention can be injected into an animal and, once injected, induces immune responses which protect the animal from severe heartwater when exposed to infection with *Cowdria ruminantium* rickettsiae.

In a preferred embodiment of the subject invention, there is further provided for the rickettsia to be the Mbizi strain of *Cowdria ruminantium*. The rickettsia of the subject invention was deposited with the National Bank for Industrial Micro-organisms and Cell Culture in Sofia, Bulgaria (NBIMCC) located at 125, Tsarigradskochausse Blvd., Block 2, 1113 Sofia, Bulgaria under accession number 3568 on Nov. 2, 1998.

In a specific embodiment, the rickettsia are cultured, using methods known in the art, in bovine endothelial cells and harvested from the cultured supernate by centrifugation. The harvested rickettsiae are inactivated by suspension in a solution of β-propiolactone in phosphate buffered saline at a temperature of 4° C. for a period of 2.5 hours. The inactivated rickettsiae can be stored frozen at a temperature of between −40° C. to −80° C., prior to mixing with an adjuvant.

In a preferred embodiment, the pathologically inactivated rickettsiae are mixed with an adjuvant. The concentration of rickettsiae is approximately 300 μg protein per milliliter of phosphate buffered saline mixed with about 1 ml of adjuvant. The vaccine may be stored on ice until ready for use. The vaccine can be injected, subcutaneously, preferably in the shoulder region of the animal.

The invention further extends to a method of producing a vaccine for use against heartwater. In a specific embodiment, this method comprises the steps of:

(a) isolating and culturing pathologically active rickettsiae in a suitable culture medium;

(b) harvesting the rickettsiae from the culture medium once the concentration of rickettsiae in said culture medium has reached a predetermined minimum or until the happening of a predetermined event;

(c) rendering the rickettsiae pathologically inactive; and (d) mixing the pathologically inactive rickettsiae with a suitable adjuvant.

The invention also provides for a method of immunizing mammals against heartwater comprising inoculating an animal, preferably cattle, alternatively sheep, goats, deer, springbok and antelope, further alternatively other susceptible ruminants, subcutaneously, preferably in the shoulder region, with a vaccine as described above and reinoculating the animal after the first inoculation, preferably between 4 and 8 weeks after the first inoculation.

DETAILED DISCLOSURE OF THE INVENTION

The subject invention provides materials and methods for inducing a protective immune response against heartwater. In accordance with this invention, there is provided a vaccine against heartwater comprising cultured inactivated *Cowdria ruminantium* rickettsiae mixed with a suitable adjuvant. The vaccine of the subject invention can be injected into an animal and, once injected, induces immune responses which protect the animal from severe heartwater when exposed to infection with *Cowdria ruminantium* rickettsiae.

Specifically exemplified herein is the use of the Mbizi strain of *Cowdria ruminantium*. Preferably, the Mbizi strain is formulated with an appropriate adjuvant and then used as a vaccine composition.

The Mbizi strain of *Cowdria ruminantium* accession No. 3568, has been deposited for the purposes of this patent application under conditions that assure that access to this culture is available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

In a specific embodiment, the rickettsiae are cultured, using methods known in the art, in bovine endothelial cells and harvested from the cultured supernate by centrifugation. The pelletised organisms are then resuspended and washed in phosphate buffered saline after which they are rendered pathologically inactive by washing for 2.5 hours in a 0.4% by volume of β-propiolactone in phosphate buffered saline at 4° C. After inactivation the rickettsiae can be frozen to between –40° C. and –80° C. Either prior to freezing or after freezing, the protein content of the harvested organisms can be determined using the Lowry method.

When its use is required, the vaccine is prepared by mixing the thawed organisms with phosphate buffered saline to give a dosage unit of about 300 µg protein per ml phosphate buffered saline. The vaccine may be stored in this form on ice and it can be injected subcutaneously over the shoulder area of the animal. A booster injection can be administered in the same region between about 4 and 8 weeks after the initial inoculation. The injected animal is considered to be immune to heartwater after a further 4 weeks have elapsed.

Materials and Methods
Sheep, Inoculations and Monitoring.

Merino or Merino-Dorper-cross sheep (6 months old) were used in vaccine trials. These sheep were obtained from heartwater-free farms in Ruwa and Mazowe in the regions of the highveld of Zimbabwe, where both Amblyomma tick vectors and heartwater have not been recorded since the start of veterinary surveillance around the turn of the century. Although they were free of heartwater, some sheep were serologically positive (false positives) on *C. ruminantium* antigen immunoblots due to cross-reactions with agents such as Ehrlichia species. It has previously been shown that such sheep are fully susceptible to heartwater challenge. To avoid any bias, such false positive sheep were distributed equally into vaccinated and control groups. The vaccinated groups were inoculated with the inactivated organisms with adjuvant and the control groups with adjuvant mixed with phosphate buffered saline (PBS; $NaH_2PO_4 2H_2O$, 0.0028 M; $Na_2HPO_4$; 0.0072M; NaCl, 0.15 M; pH 7.3), except in the adjuvant selection trial described below. All inoculations were performed by the subcutaneous route, and any reaction at the injection site was recorded. In addition, any clinical reaction following vaccination was also recorded. Following challenge with a lethal dose of *C. ruminantium* (intravenous or via ticks), the rectal temperature of each sheep was recorded daily, and protection was determined by comparing differences in rickettsemia, time to death, and mortality rates between the vaccinated and control sheep. However, the ultimate indicator of protection was the level of mortality in the vaccinated compared to control groups. Clinical signs, though recorded, were not used as a parameter of protection since they are not specific for heartwater and can vary widely from peracute to mild forms of the disease.

Preparation of inactivated *C. ruminantium* Organisms for Vaccination

The Mbizi strain of *C. ruminantium* was inactivated was β-propiolactone as described above. The inactivated organisms were quantified by staining with acridine orange, and by the Lowry method of protein estimation, and stored at –40° C. for use in vaccine trials.

Following are examples which illustrate procedures for practicing the invention. These examples should not be construed as limiting. All percentages are by weight and all solvent mixture proportions are by volume unless otherwise noted.

EXAMPLE 1

Freund's Adjuvant Trials

Six sheep were vaccinated three times at 3–4 week intervals with inactivated Mbizi strain (200 µg of antigen) in combination with complete Freund's adjuvant(cFA) for the first inoculation and with incomplete FA for the remaining two booster inoculations. Six control sheep were inoculated similarly with the adjuvant mixed with PBS. Then, 4 weeks after the last inoculation, simultaneously, the six control and six *C. ruminantium* (Mbizi) vaccinated sheep were challenged by the intravenous route with a lethal dose containing $1 \times 10^7$ *C. ruminantium* (Mbizi) viable organisms from cell culture. Protection against challenge was determined by analysing for significant differences in the brain endothelial cell rickettsiosis (t-test or Mann-Whitney rank sum test on arc sine square root transformed percentage infection data) and mortality (two-tailed Fisher exact test) of the vaccinated and control groups. Analysis of brain cell rickettsiosis was performed by persons blinded to the sample groupings.

The efficacy of the Mbizi strain of *C. ruminantium* in combination with cFA was evaluated. Prechallenge reciprocal Inmunoblot antibody titres, ranged between $2 \times 10^4$ and $1 \times 10^5$ in the vaccinated sheep. The control sheep had background titres of $1 \times 10^2$ to $4 \times 10^2$.

In response to homologous *C. ruminantium* challenge, one of six Mbizi vaccinated sheep died compared to death of all control sheep (Table 1). Also, brain cell rickettsiosis was higher in the control sheep than in the vaccinated sheep.

TABLE 1

Freund's adjuvant trials: incorporation of the Mbizi strain of
C. ruminantium into an inactivated vaccine

| Group and C. ruminantium strain, with number of sheep in parentheses | Prechallenge anti- C. ruminantium end titres | Average percentage rickettsiosis per 500 endothelial cells per brain biopsy | Response to intravenous challenge |
|---|---|---|---|
| Controls, Mbizi, (6) | 1:100 to 1:400 | 2.19 ± 1.42 | 6 of 6 sheep died |
| Vaccinated, Mbizi (6) | 1:20000 to 1:100000 | 0.23 ± 0.51 | 1 of 6 sheep died |

EXAMPLE 2

Protection Against Heartwater Strains from Different Geographical Locations

To evaluate whether the inactivated vaccine can protect against C. ruminantium strains from different geographical locations, 24 sheep were vaccinated with inactivated C. ruminantium (Mbizi) vaccine and another 24 sheep were inoculated with adjuvant mixed with PBS as described above. Then, 4 weeks after the last booster inoculation, six vaccinated and six control sheep were challenged by the intravenous route with $1\times10^7$ to $3\times10^7$ live cell cultured organisms of either the Isiolo (from Kenya), Welgevonden (from South Africa) or Beatrice (from Zimbabwe) strain. As controls for the heterologous challenge, six vaccinated and six control sheep were challenged similarly with the $1\times10^7$ homologous Mbizi strain organisms. Following challenge, the sheep were monitored as described above.

Sheep vaccinated with the C. ruminantium (Mbizi) inactivated vaccine and challenged with the heterologous Beatrice, Isiolo or Welgevonden strains had 1 of 6, 0 of 6 and 0 of 6 deaths, compared to 5 of 6, 2 of 6, and 3 of 6 deaths in their respective control groups. Challenge with the homologous Mbizi strain resulted in death of 2 of 6 vaccinated and 4 of 6 control sheep. Whilst, taken individually, there was only significant protection using the Beatrice challenge (P=0.041), overall, 3 of 24 vaccinated sheep died of heartwater challenge in comparison to death of 14 of 24 control sheep (P=0.002), suggesting that (Mbizi)-vaccinated animals are protected against challenge with diverse strains of C. ruminantium.

These data showed that the Mbizi strain of C. ruminantium can be incorporated into the vaccine as appropriate to overcome lack of cross-protection between an inactivated C. ruminantium vaccine strain and local strains from different geographical regions.

EXAMPLE 3

Selection of Adjuvants

Five adjuvants with acceptable safety for use in vaccines were tested in the inactivated C. ruminantium vaccine to replace the commercially unacceptable cFA. These were alhydrogel (SergeantPulp, Clifton, N.J., USA), biocine (Chiron,Emeryville,Calif., USA), incomplete Freund's adjuvant (Sigma, St. Louis, Mo., USA), Quil A (Superfos, Denmark) and Montanide ISA 50 (Seppic, Paris, France). Each adjuvant was mixed with200 μg of the inactivated C. ruminantium (Mbizi) organisms as recommended by the manufacturers. The respective vaccines were then inoculated subcutaneously, with two booster vaccinations given at 4-week intervals. Prechallenge antibody titres to C. ruminantium were determined by immunoblotting for all sheep (Mahan, S. M., N. Tebele, D. Mukwedeya et aL [1993] J. Clin. Microbiol. 31:2729–2737]. Then, 4 weeks after the last vaccination, all sheep were challenged with $1\times10^7$ viable C. ruminantium (Mbizi) organisms by the intravenous route. A group of five untreated control sheep were included to confirm the virulence of the challenge. The sheep were monitored routinely and the number of mortalities in each adjuvant group was compared and evaluated for statistical significance as described above. The adjuvant/C. ruminantium vaccine combinations that induced the mildest disease symptoms and had the highest number of surviving sheep were selected for further evaluation.

The efficacies of the inactivated C. ruminantium (Mbizi) vaccines prepared in combination with five different adjuvants were compared with each other and with the vaccine prepared in cFA. The adjuvant efficacy was determined from the severity of clinical disease and the percentage mortality in each group in response to homologous intravenous challenge. The results are presented in Table 2. All sheep vaccinated with inactivated C. ruminantium developed antibodies, with cFA consistently inducing the highest titres. In response to challenge, sheep vaccinated with inactivated C. ruminantium in combination with cFA, Montanide ISA 50 or Quil A had survival rates of 57%, 50% and 43%, respectively. Sheep vaccinated with inactivated C. ruminantium in combination with alhydrogel, biocine or incomplete Freund's adjuvant exhibited more severe clinical signs (anorexia, depression and respiratory distress) and lower survival rates of 29%, 20% and 16%, respectively. The same challenge killed 60% of untreated control sheep, and the survivors in this group were acutely ill, demonstrating that the challenge was virulent. Based on observed differences in the clinical symptoms of heartwater disease and survival rates, Montanide ISA 50 and QS-21 (the major immunogenic component of Quil A) were selected for further evaluation.

Further evaluation of the inactivated vaccine in two adjuvants,Montanide ISA 50 and QS-21 (the major immune-enhancing component of Quil A), was conducted using natural tick challenge at the Vlakfontein Farm in Zimbabwe. Two groups of seven sheep each were vaccinated three times subcutaneously with the inactivated organisms in Montanide ISA 50 or QS-21, and another two groups were inoculated with the respective adjuvant mixed with PBS. Then, 4 weeks after the final inoculation, the sheep were subjected to natural C. ruminantium challenge by exposure to ticks at the heartwater-endemic Vlakfontein Farm. Prior to challenge, antibody titres to C. ruminantium were determined by immunoblotting. The sheep were monitored routinely, and weekly tick counts were performed on all sheep to determine the level of A. hebraeum tick challenge. Differences in mortalities between the vaccinated and control sheep were evaluated for statistical significance as described previously.

Twenty-eight sheep vaccinated with inactivated C. ruminantium (Mbizi) in combination with either Montanide ISA 50 or QS-21, or the respective adjuvants alone, were challenged naturally by A. hebraeum ticks at the Vlakfontein Farm. Prechallenge antibody titres to C. ruminantium are shown in Table 3. The tick challenge experienced by these sheep was uniform with the nymphal ticks providing a higher challenge than adults (data not shown). In response, clinically the control sheep suffered a more severe course of heartwater disease than the vaccinated sheep. Of seven controls, six, and of seven sheep vaccinated with inactivated C. ruminantium using the Montanide ISA 50, adjuvant, one, died of heartwater. These mortalities were significantly different (Table 3; P=0.029 1). In contrast, five of seven control sheep and three of seven sheep vaccinated using QS-21 adjuvant died of heartwater (Table 3). Although more sheep survived in the QS-21/C. ruminantium vaccinated group than the QS-21 adjuvant control group, there was no significant difference in number of mortalities between these two groups.

TABLE 2

Vaccine efficacy (Mbizi vaccine) using different adjuvants: homologous challenge

| C. ruminantium and adjuvant | Number of sheep | Prechallenge antibody titres | Number of survivors after challenge (%) |
|---|---|---|---|
| Alhydrogel | 7 | 1:20000 to 1:200000 | 2/7 (29) |
| Biocine | 5 | 1:5000 to 1:100000 | 1/5 (20) |
| Montanide ISA 50 | 6 | 1:5000 to 1:40000 | 3/6 (50) |
| Quil A | 7 | 1:10000 to 1:100000 | 3/7 (43) |
| Incomplete Freund's | 6 | 1:10000 to 1:20000 | 1/6 (17) |
| Complete Freund's | 7 | 1:200000 to 1:400000 | 4/7 (57) |
| Untreated Control | 5 | ND | 2/5 (40) |

ND, antibody titres were not determined in this group.

TABLE 3

Vaccine efficacy (Mbizi vaccine) using Montanide ISA 50 (ISA 50) and QS-21 adjuvant against natural field tick challenge

| Group and adjuvant with number of sheep in parentheses | Prechallenge Western Blot end titres | Response to challenge |
|---|---|---|
| Controls, ISA 50, (7) | 1:100 to 1:1000 | 6 of 7 sheep died |
| Vaccinated, ISA 50, (7) | 1:40000 to 1:160000 | 1 of 7 sheep died |
| Controls, QS-21, (7) | 1:100 to 1:1000 | 5 of 7 sheep died |
| Vaccinated, QS-21, (7) | 1:20000 to 1:40000 | 3 of 7 sheep died |

There was a significant difference in mortalities (P = 0.0291) between the vaccinates and controls of the Montanide ISA 50 adjuvant group. However there was no significant difference in mortalities between the vaccinates and controls of the QS-21 adjuvant group.

After inoculation with the vaccine in cFA or inoculation with the adjuvant alone, a long-lasting swelling/granuloma usually formed. Such a swelling was present throughout the trials which were of 4–6 month duration. Usually, after inoculation with cFA a febrile reaction (>40.5° C.) was observed for 1 day which subsided without treatment.

In contrast, a transient swelling occurred after inoculation with Montanide ISA 50 which lasted for 4 weeks in some sheep (2 of 20) but subsided during this period in the rest. No reactions were observed with inoculations of the QS-21 adjuvant. No other adverse effects were observed following vaccine administration in combination with the various adjuvants.

The adjuvant selection trial results suggest that alhydrogel, biocine and incomplete FA are not optimal adjuvants for use in an inactivated vaccine against heartwater. These adjuvants are recognized as potent stimulators of humoral responses. Humoral responses on their own are not believed to play a significant role in protection against heartwater, although antisera from immune mice and bovines are capable of neutralizing C. ruminantium infection in bovine endothelial cells in vitro. Protective immune mechanisms against heartwater likely require the activation of T cell responses. It has been demonstrated that a CD4+T cell response is induced in cattle that are vaccinated with the inactivated C. ruminantium organisms in cFA and that these cells proliferate when stimulated with lysates of C. ruminantium and produce IFN-γ which has been shown to be inhibitory for growth of C. ruminanium (Mahan, S. M. et al. [1994] *Infect. Immun.* 62:747–750; Mahan, S. M. et al. [1996] *Parasite Immunol.* 18:317–324; and Totté et al. [1996] *Vet. Immunol. Immunopathol.* 53:61–71).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition comprising a biologically pure culture of the Mbizi strain of *Cowdria ruminantium*, having NBIMCC accession no. 3568.

2. The composition according to claim 1, further comprising an adjuvant.

3. A method for rising or inducing an immune response against rickettsiae in an animal, said method comprising immunizing said animal with a composition comprising the inactivated Mbizi strain of *Cowdria ruminantium*, having NBIMCC accession no. 3568, wherein said composition further comprises an adjuvant.

4. The method according to claim 3, wherein said animal is a mammal.

5. The method according to claim 4, wherein said mammal is a ruminant.

6. A method for protecting an animal against heartwater, said method comprising administering to said animal an effective amount of a composition comprising the inactivated Mbizi strain of *Cowdria ruminantium*, having NBIMCC accession no. 3568, wherein said composition further comprises an adjuvant.

7. The method according to claim 6, wherein said animal is a mammal.

8. The method according to claim 7, wherein said mammal is a ruminant.

* * * * *

UNITED STATES PATENT AND TRADEMARK OFFICE
CERTIFICATE OF CORRECTION

PATENT NO. : 6,342,230 B1
DATED : January 29, 2002
INVENTOR(S) : Suman M. Mahan, Anthony F. Barbet, Michael J. Burridge and Gillian E. Smith It is certified that error appears in the above-identified patent and that said Letters Patent is hereby corrected as shown below:

Column 1,
Line 7, "InternationalDevelopment" should read -- International Development --.

Column 4,
Line 40, "adjuvant(cFA)" should read -- adjuvant (cFA) --.

Column 5,
Line 61, "(SergeantPulp)" should read -- (Sergeant Pulp) --.
Line 65, "with200" should read -- with 200 --.

Column 6,
Line 4, "et aL" should read -- et al. --.
Line 40, "adjuvants,Montanide" should read -- adjuvants, Montanide --.

Column 7,
Line 3, "P=0.029 1)." should read -- P=0.0291). --.

Column 8,
Line 33, "rising" should read -- raising --.

Signed and Sealed this

Eighteenth Day of June, 2002

*Attest:*

*Attesting Officer*

JAMES E. ROGAN
*Director of the United States Patent and Trademark Office*